United States Patent
Pal et al.

(10) Patent No.: US 9,820,968 B2
(45) Date of Patent: Nov. 21, 2017

(54) ANTI-LEUKEMIC AGENT USEFUL FOR INDUCING DIFFERENTIATION IN MYELOID LEUKEMIA CELLS

(71) Applicant: Council of Scientific and Industrial Research, Rafi Marg, New Delhi (IN)

(72) Inventors: Pooja Pal, Lucknow (IN); Savita Lochab, Lucknow (IN); Jitendra Kumar Kanuajiya, Lucknow (IN); Sabyasachi Sanyal, Lucknow (IN); Arun Kumar Trivedi, Lucknow (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/024,181

(22) PCT Filed: Feb. 28, 2014

(86) PCT No.: PCT/IN2014/000131
§ 371 (c)(1),
(2) Date: Mar. 23, 2016

(87) PCT Pub. No.: WO2015/044950
PCT Pub. Date: Apr. 2, 2015

(65) Prior Publication Data
US 2016/0228410 A1    Aug. 11, 2016

(30) Foreign Application Priority Data
Sep. 24, 2013    (IN) .......................... 2807/DEL/2013

(51) Int. Cl.
C07D 311/04      (2006.01)
A61K 31/4025     (2006.01)

(52) U.S. Cl.
CPC ............................... A61K 31/4025 (2013.01)

(58) Field of Classification Search
CPC .................................................. C07D 311/04
USPC ....................................................... 549/398
See application file for complete search history.

(56) References Cited

U.S. PATENT DOCUMENTS 7,595,342 B2 *  9/2009  Hansen .................. A61K 33/24
                                                           514/574

FOREIGN PATENT DOCUMENTS

WO        2009037001    *   3/2009

OTHER PUBLICATIONS

Gara et al., Current Medicinal Chemistry (2013), 20(33), 4177-4184.*
Makker et al., Fertility and Sterility (2009), 91(6), 2298-2307.*
International Search Report for International Application No. PCT/IN2014/000131 dated Jul. 29, 2014 (3 pages).
Bandyopadhyay et al. "Chlorogenic acid inhibits Bcr-Abl tyrosine kinase and triggers p38 mitrogen-activated proteien kinase-dependent apoptosis in chronic myelogenous leukemic cells." Blood vol. 104, (2004) pp. 2514-2522.
Estrove et al. "Resveratrol blocks interleukin-1B-induced activation of the nuclear transcription fractor NF-kb, inhibits proliferation, casuses S-phase arrest and induces apoptosis of acute myeloid leukemia cells." Blood, vol. 102, No. 3 (2003) pp. 987-995.
Girl et al. "Antimutagenic effects of centchroman—a contraceptive and a candidate drug for breast cancer in multiple mutational assays." Mutagenesis vol. 14, No. 6. (1999) pp. 613-619.
Ikeda et al. "Triterpenoid CDDO—Im downregulates PML/RARa expression in acute promyelocytic leukemia cells." Cell Death And Diff. vol. 12 (2005) pp. 523-531.
Jacquel et al. "Imatinib induces mitrochondria-dependent apoptosis of the Bcr-Abl positive K562 cell line and its differentiation towards the erythroid lineage." The Faseb Journal. (2003) 24 pages.
Jing et al. "Benzodithiophenes Induces Differentiation and Apoptosis in Human Leukemia Cells." CANCER RES. vol. 65 No. 17. (2005) pp. 7847-7855.
Koschmieder et al. "CDDO induces granulocytic differentiation of myeloid leukemic blasts through translational up-regulation of p42 CCAAT enchancer binding protein alpha." Blood. vol. 110. (2007) pp. 3695-3705.
Krug et al. "Maintenance therapy in acute myeloid leukemia revisited: will new agents rekindle an old interest?" Current Opin in Hematology. vol. 17. (2010) pp. 85-90.
Kumar et al. "Effect of concurrently coadministered drugs on pharmacokinetic/pharmacodynamic profile of centchroman, anonsteroidal oral contraceptive, in rats." Contraception vol. 74. (2006) pp. 165-173.
Lerga et al. "Regulation of c-Myc and Max in Megakaryocytic and Monocytic-Macrophagic Differentiation of K563 Cells induced by Protein Kinase C Modifiers: c-Myc is Down-regulated but does not inhibit differentiation." Cell Growth & Differntiation. vol. 10. (1999) pp. 639-654.

(Continued)

*Primary Examiner* — Niloofar Rahmani
(74) *Attorney, Agent, or Firm* — Merchant & Gould P.C.

(57) ABSTRACT

The present invention provides the compound Ormeloxifene [3, 4-trans-2,2-dimethyl-3-phenyl-4-p-(beta-pyrrolidinoethoxy) phenyl-7-methoxy chroman] as useful in inducing differentiation in wide range of myeloid leukemias including acute promyelocytic leukemia, acute myeloid leukemia and chronic myeloid leukemia where block in differentiation is common feature. Ormeloxifene induced differentiation that is marked by increase in differentiation marker proteins like C/EBPα and surface proteins such as cd11b and granulocyte colony stimulating factor receptor (GCSFr). Differentiated cells having neutrophil like morphology were observed when treated with 1.0 uM to 7.5 uM ORM which clearly indicates that ORM can induce differentiation in myeloid leukemia cells. At higher doses (5 uM to 7.5 uM) there is early onset of myeloid differentiation (24 to 48 h) with reduced no. of cells which is likely due to apoptotic effects of ORM at higher does. In contrary, lower doses (1 uM) induce differentiation after longer duration (6-15 days) with quite reduced apoptotic effect.

7 Claims, 9 Drawing Sheets

(56) References Cited

OTHER PUBLICATIONS

Ma et al. "Novel Agents on the Horizon for Cancer Therapy." CA Cancer J. Clin. Vo. 59. (2009) pp. 111-137.
Mao et al. "Induction of apoptosis by shikonin through a ROS/JNK-mediated process in Bcr/Abl-positive chronic myelogenous leukemia (CML) cells." Cell Research vol. 18. (2008) pp. 879-888.
Misra et al. "Centchroman—a non-steriodal anti-cancer agent for advanced breast cancer: phase-II study." Int. J. Cancer. vol. 43. (1989) pp. 781-783.
Mukhopadhyay. "Anticlastogenic effects of centchroman and its enantiomers in swiss albino mice. I: Acute study and their comparison with tamoxifen." Cancer Letters. vol. 144 (1999) pp. 137-143.
Pal et al. "2-D gel electrophoresis-based proteomic analysis reveals that ormeloxifen induces G0-G1, growth arrest and ERK-mediated apoptosis in chronic myeoloid leukemia cells K562." Protemics. vol. 11 (2011) pp. 1517-1529.
Singh. "Centchroman, a selective estrogen receptor modulator, as a contraceptive and for the management of hormone-related clinical disorders." Medicinal Res. Rev. vol. 21, No. 4. (2001) pp. 302-347.
Waxman. "Differentiation therapy in acute myelogenous leukemia (non-APL)." Leukemia. vol. 14. (2000) pp. 491-496.
Xia et al. "Boswellic acid acetate induces apoptosis through caspase-mediated pathways in myeloid leukemia cells. " Molecular Cancer Tehera. vol. 4 (2005) pp. 381-388.

\* cited by examiner

FIG. 3a:
Gimesa
Staining

K562 unin 12 days    1uM ORM 12days    5uM ORM 72h    DMSO 12 days

FIG. 3b:
NBT Staining

K562 uninduced    7.5uM ORM 24h    7.5uM ORM 48h

1uM ORM 6 days    5uM ORM 72h

ANTI-LEUKEMIC AGENT USEFUL FOR INDUCING DIFFERENTIATION IN MYELOID LEUKEMIA CELLS

This application is a National Stage Application of PCT/IN2014/000131, filed 28 Feb. 2014, which claims benefit of Serial No. 2807/DEL/2013, filed 24 Sept. 2013 in India and which applications are incorporated herein by reference. To the extent appropriate, a claim of priority is made to each of the above disclosed applications. The following specification particularly describes the invention and the manner in which it is to be performed:

FIELD OF INVENTION

Present invention relates to an anti-leukemic agent useful for inducing differentiation in myeloid leukemia cells. More particularly the present invention relates to Ormeloxifene (here after abbreviated as ORM) that induces differentiation in myeloid leukemia cells. ORM has been tested and licensed as a birth control pill, as well as in the treatment of dysfunctional uterine bleeding. The present invention provides an insight into new role of ORM in inducing differentiation in myeloid leukemia where block in differentiation is a common feature.

BACKGROUND OF THE INVENTION

Figure 1A:
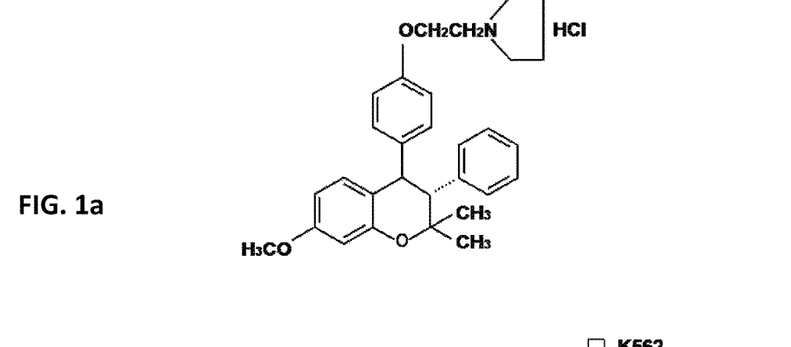

Myeloid leukemia is a hematologic malignancy characterized by the block in differentiation and abnormal proliferation of clonal myeloid blast cells. Despite extensive clinical research with numerous combinations of cytotoxic agents the overall prognosis of myeloid leukemia patients remains poor, thus hunt for better effective agents is ongoing (U. Krug, et. al.; Curr Opin Hematol, 2010, 17(2):85-90; W. W. Ma, et. al.; Cancer J Clin, 2009, 59(2), 111-37). Ormeloxifene (3,4-trans-2,2-dimethyl-3-phenyl-4-p-(beta-pyrrolidinoethoxy)phenyl-7-methoxychroman), also known as Centchroman, the chemical structure of which is shown in FIG. 1a, is a potent non-steroidal selective estrogen receptor modulator (SERM) used as oral contraceptive for birth control. ORM suppresses the receptors in the reproductive organs like the ovaries, uterus and breasts while it stimulates the estrogen receptors of organs like the bones (A. Mukhopadhyay et. al.; Cancer Lett, 1999, 144(2),137-43; M. M. Singh, Med Res Rev, 2001, 1(4), 302-47; V Kumar et. al.; Contraception, 2006, 74(2), 165-73).

Substantial evidence has been amassed to support the premise that ORM has potential anticancer activity (N. C. Misra et. al.; Int J Cancer, 1989, 43(5), 781-3). So, while it acts as a birth control pill it can prevent breast cancers, uterine cancers and stimulate the formation of new bones (M. M. Singh, Med Res Rev, 2001,21 (4):302-347). In a published study, Mishra et. al, evaluated the role of ORM in breast cancer patients. Apparently, treatment with ORM was evaluated in 4 male and 75 female patients with advanced breast cancer. The overall response rates including both male and female cases, was 40.5%. Among the female patients, the overall response rate was 38.7%. One of the 4 male patients showed a complete response and 2 showed partial responses. The responses were more marked for bone, pulmonary, soft tissue, skin and lymph-node metastases than for liver metastases (N. C. Misra, et. al.; Int J Cancer, 1989, 43(5), 781-3). Furthermore, ORM can reduce the mutagenic effects of known genotoxic compounds dimethylbenz[a]anthracene (DMBA), cyclophosphamide (CP), mitomycin C (MMC) and ethyl methanesulfonate (EMS) in Salmonella. These protective activities of ORM against the known positive mutagens in the Salmonella may be due to induction of apoptosis by ORM, which leads to the elimination of cells damaged by these mutagens from the cell population (A. K. Giri, et. al.; Mutagenesis, 1999, 14 (6):613-620). Arrested differentiation and increased cell proliferation due to transformation of immature hematopoietic cells is the hallmark of leukemia. This prolongs the growth factor-independent survival of leukemic progenitors by inhibiting the apoptosis. Therefore, agents that can eliminate transformed cells by induction of apoptosis and differentiation in arrested cells rather than merely slowing down their proliferation may have larger therapeutic potential. The increased understanding of apoptosis pathways has directed attention to components of these pathways as potential targets for therapeutic agents (D. G. Tenen, Nat Rev Cancer, 2003, 3(2):89-101). Indeed, an increasing number of previously identified therapeutic agents including, retinoids, vitamin $D_3$ analogues, Benzothipopenes, Chlorogenic acid, Guggulsterone, Shikonin, Boswelic Acid, CDDO, Resveratrol and others were found to enhance apoptosis and induce differentiation in a variety of premalignant or malignant leukemia cell types in vitro and in a few animal models in vivo (G. Bandyopadhyay et. al.; Blood, 2004, 104 (8):2514-2522; Z. Estrov et. al.; Blood, 2003, 102(3):987-995; Y. Jing, et. al.; Cancer Res, 2005, 65(17) 7847-7855; X. Mao et. al.; Cell Res 2008, 18(8):879-888; L. Xia et. al.; Mol Cancer Ther, 2005, 4(3):381-388). With this pre-context, in our earlier study we have showed the anticancer activity of ormeloxifene in myeloid leukemia cells. We have shown that ormeloxifene at an $IC_{50}$ of 7.5 uM induces apoptosis in HL60, U937 and K562 cells (P. Pal, et. al; Proteomics, 2011, 11 (8):1517-1529). Our studies clearly demonstrate that ormeloxifene can induce apoptosis in myeloid leukemia cells. Most of the anticancer compounds having potential to induce apoptosis in leukemic cells have been shown to induce differentiation at subapoptotic doses (S. Koschmieder, et. al.; Blood, 2007, 110 (10):3695-3705). Therefore, here we sought to investigate if ORM has also any differentiation inducing potential in myeloid leukemia cells and thus in the present invention we have investigated the new role of non-steroidal anti contraceptive "Ormeloxifene" in myeloid leukemia.

Earlier P Pal et al reported that this antileukemic agent ORM induces apoptosis (P. Pal et al.; Proteomics, 2011, 11 (8):1517-1529) at a concentration of 7.5 uM. However results of present invention reveals that ORM at a concentration of 7.5 uM also induces differentiation when used for a shorter time period. Moreover ORM at a concentration of 1.0 uM also induces differentiation when treated for longer time period in myeloid leukemia cells. Therefore ORM is advantageous over other antileukemic agents which either induce apoptosis or differentiation alone. This antileukemic agent induces myeloid differentiation which is marked by induction of myeloid differentiation markers.

OBJECTS OF THE INVENTION

Therefore one of the objects of present invention is to provide an anti-leukemic agent that can induce differentiation in myeloid leukemia cells.

Another object of the present invention is to provide new use of a non-steroidal anti contraceptive Ormeloxifene as an anti leukemic agent.

SUMMARY OF THE INVENTION

Accordingly the present invention provides an anti-leukemic agent useful for inducing differentiation in leukemia cell, said anti-leukemic agent is a non-steroidal anti contraceptive drug Ormeloxifene having the structural formula as shown in FIG. 1a.

In an embodiment of present invention the anti-leukemic agent Ormeloxifene useful for induction of differentiation in leukemia cell is dose dependent, preferably at a dose ranging 1 uM-7.5 uM.

In yet another embodiment of present invention the said anti-leukemic non steroidal drug ormeloxifene induces granulocytic differentiation in K562, a leukemia cell line.

In another embodiment of present invention the non-steroidal anti contraceptive drug Ormeloxifene promotes myeloid differentiation in HL60 and U937, a promyelocyte and myelomonocyte leukemia cell line.

Accordingly, the present invention provides new use of clinically validated drug Ormeloxifene as an anti-leukemic agent in vitro, useful for the management or prevention or treatment or cure of human leukemia One embodiment of the present invention provides the compound Ormeloxifene as useful in inducing differentiation in wide range of myeloid leukemias including acute promyelocytic leukemia, acute myeloid leukemia and chronic myeloid leukemia where block in differentiation is common feature.

Further embodiment of the present invention provides Ormeloxifene induced differentiation that marked by increase in differentiation marker proteins like C/EBPα and surface proteins such as cd11b are granulocyte colony stimulating factor receptor (GCSFr)

BRIEF DESCRIPTION OF DRAWINGS

FIG. 1: ORM induces cell toxicity in myeloid leukemia cells: (a) Chemical structure of ormeloxifene. (b) Cell viability as determined by MTT colorimetric assay, shows % viable cells after myeloid leukemia cells were treated with increasing doses of ormeloxifene. Assay was performed on 3 replicates for each treatment and repeated twice. 50% growth inhibition was observed at around 7.5 uM.

FIG. 3: ORM induces differentiation like morphology in K562 cells: (a) Giemsa staining of K562 cells treated with 1 uM ORM for 12 days and 5 uM for 72 hrs shows neutrophil like morphological changes. (b) NBT staining of K562 cells after treatment with 7.5 uM ORM for 24 h and 48 h, 5 uM ORM for 72 h and 1 uM ORM for 6 days shows purple blue colouration as compared to control K562 which is indicator of NBT reduction by neutrophils.

FIG. 4: ORM induced myeloid differentiation is marked by up regulation of differentiation related markers in K562 cells: Real time PCR (RT-PCR) showing significant increase in mRNA expression of (a) cd11b (b) C/EBP epsilon (c) C/EBP alpha (d, e) GCSFr (f, g) Reverse transcriptase-PCR shows the marked increase in the level of GCSFr.

FIG. 6: ORM induces myeloid differentiation in primary cells isolated from CML patients PBMCs were isolated from patient samples and were analyzed by FACS for cd11b positive cells. There was increase in the expression of (a) cd11b and (b) cd114 after treatment of cells with 1 uM ORM for 24 h and 48 h (c) Graphically shows percentage of cd11b and cd114 positive cells in FACS analysis.

FIG. 7: ORM at 1 uM dose induces differentiation like morphology both in HL60 and U937 cells: (a) HL60 and (b) U937 cells were treated with 1 uM ORM for 12 and 15 days and there was change in the morphology of cells by decrease in the nuclear and cytoplasmic ratio and formation of multilobed nuclei which is typical for neutrophilic differentiation.

DETAILED DESCRIPTION OF THE INVENTION

The compounds, methods, compositions and activity testing illustrated in details as follows:

1. Cell culture and plasmids: HL60, U937 and K652 cells were cultured in RPMI1640 supplemented with 10% FBS and 1% antimycotic and antibiotics. Cells were cultured in 5% $CO_2$ humified incubator at 37° C.

2. MTT assay: Post 6 h synchronization, $1 \times 10^4$ cells per well were incubated at 37° C. in 96-well plastic plates with test drugs containing 10% FBS in an environment of 5% humified $CO_2$. After 48 hrs, cell viability was assessed by the ability of metabolically active cells to reduce tetrazolium salt (XTT) to coloured formazan compounds. The absorbance of the samples was measured with a specific enzyme-linked immunosorbent assay (ELISA) reader at 560 nm.

3. Giemsa staining: Giemsa stain is used to differentiate nuclear and cytoplasmic morphology of blood cells. After induction with 1 uM ORM for 12 days cells were cytospun on slides at 800 rpm for 5 min and were air dried. Cells were stained with Giemsa stain (Sigma) as per manufacturer's protocol. Cells were visualized microscopically for the morphological changes.

4. NBT assay: The NBT Assay relies on the accumulation of blue black formazan precipitate. The membrane permeable, water soluble, yellow NBT is reduced to blue black formazan by $O^-_2$, which is generated by activated neutrophils/phagocytes, typically by PMA. PMA activates NADPH oxidase by enhancing protein kinase C (PKC) and thus stimulates production of ROS (reactive oxygen species). After induction with 7.5 uM ORM for 24 h and 48 hr and with 1 uM ORM for 6 days cells were incubated in NBT solution for 15 min. at 37° C. Cells were washed with PBS and were resuspended in 500 ul PBS and cytospun on slides and stained with safranin O for 1 min. Number of cells showing blue-purple colouration were counted under microscope.

5. Quantitative PCR (Real Time) and semi quantitative PCR Analysis: After induction of cells with ORM for indicated time points cells were harvested and RNA was isolated using Trizol reagent. Trizol was added to $1 \times 10^6$ cells for 5 min at room temp. Lysed cells were collected in micro centrifuge tubes and shaken vigorously for 15 sec, and incubated for 3 min at RT. 200 µl of chloroform was added to each sample and incubated yet again for 5 min at RT. Cells were centrifuged at 15,000 rpm for 15 min at 4° C. Supernatant was collected in fresh tube; 1 ml isopropanol was added and incubated for 10 min at RT. Pellet was washed once with 70% ethanol and RNA concentration was quantified. Further, RNA was retro-transcribed into cDNA and subsequently used for quantitative PCR analysis on Roche Light Cycler 480 using SYBR green master mix from Applied Biosystems. Statistical analysis was performed using ΔΔCT method. Reverse transcriptase PCR was done to check the mRNA level expression of GCSFr qualitatively. RT-PCR analysis was performed using standardized PCR protocol on BioRad C1000 Thermal Cycler.

6. PBMC separation from patient sample: 10 ml peripheral blood was collected by venipuncture heparin-containing 20 ml vials. Peripheral blood mononuclear cells were isolated using density gradient centrifugation with Ficoll-Paque (1.077 g/ml). Peripheral blood was mixed in 1:1 v/v of MACS buffer and was fractionated through Ficoll-Paque. Mononuclear cells were collected from the interface, washed twice in MACS buffer and resuspended in RPMI 1640 at 37° C. in the humidified atmosphere of 5% $CO_2$.

7. FACS analysis: Cells were treated with 1 uM ORM for 24 h and 48 h. Then they were washed with 1×PBS and resuspended in antibody solution along with their respective IgG isotype control for 15-20 min as per manufacturer's protocol. Cells were washed once with PBS and were resuspended in 500 ul of PBS. After this flow cytometry was done for PI labeled cells for cd11b and cd114 differentiation markers (BD Biosciences).

Following examples are provided from the results obtained from the experiments as provided above. These should, however, not be construed to limit the scope of invention.

EXAMPLE-1

ORM Induces Growth Inhibition in Myeloid Leukemia Cells

Figure 1B:
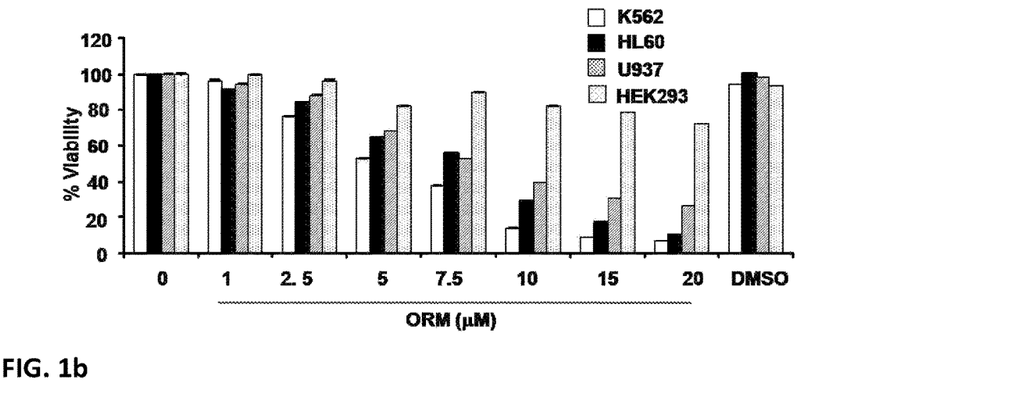

To calculate 50% growth inhibitory concentration ($IC_{50}$) of ormeloxifene, various myeloid leukemia cells (U937, HL60, K562) and HEK293T as control were assayed with different doses of ormeloxifene for cell viability in MTT Assay. ORM showed $IC_{50}$ of ~7.0 uM in leukemic cells as compared to 25 uM for 293T (FIG. 1b). Various apoptosis assays were performed in myeloid leukemia cells upon treatment with ormeloxifene that induces G0-G1 phase growth arrest and caspase mediated apoptosis in myeloid leukemia via ERK activation.

EXAMPLE-2

ORM Induces Differentiation in Myeloid Leukemia Cells

Figure 2:
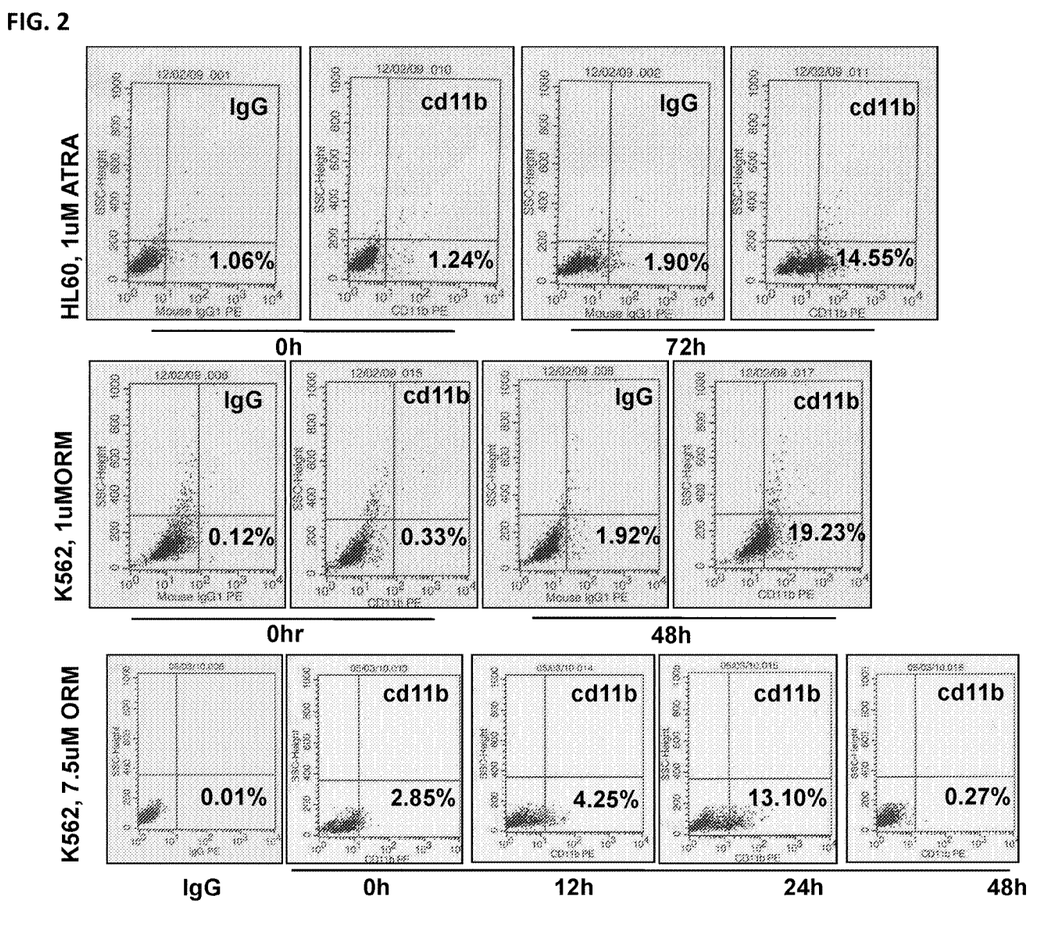
FIG. 2: ORM induces myeloid differentiation in K562 cells: Flow cytometry analysis shows that early myeloid differentiation marker cd11b is increased in ATRA treated HL60 (Upper panel; served as control for differentiation) and ORM treated K562 cells (1 uM ORM middle panel; 7.5 uM ORM lower panel) in the indicated time point.

K562 cells were treated with 1 μM (Subapoptotic dose) and 7.5 μM ORM (Apoptotic dose) for 24 h and 48 hrs. Post 24 h and 48 h treatment, cells were analyzed in FACS-flow cytometer for the presence of myeloid differentiation marker cd11b (FIG. 2). In parallel, HL60 cells were also treated with 1uM All-Trans-Retinoic Acid (ATRA) for 72 hrs which served as control for induction of differentiation. Notably, increased percentage of cells expressing CD11b markers were observed after 24 and 48 h in cells treated with 1.0 uM ORM. Reduced number of cd11b expressing cells upon induction of 7.5 uM ORM may be due to prominent apoptosis imparted by ORM at this dose. Isotype IgG-PE antibody served as negative control.

Figure 3A:
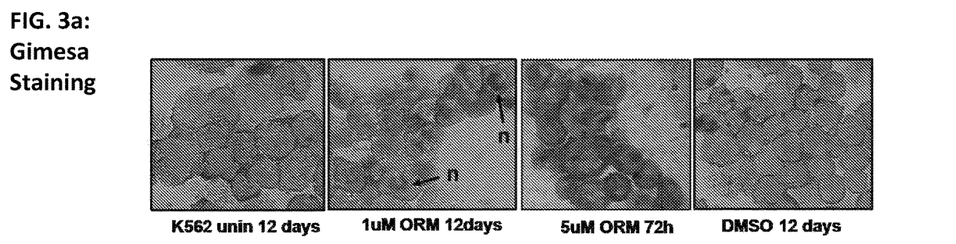

To further corroborate the differentiation inducing potential of ORM, K562 cells were again treated with 1.0 uM ORM and vehicle for 12 days followed by cytospin and staining with Giemsa for assessment of morphological changes. As shown in FIG. 3a, differentiated cells having neutrophil like morphology were observed which clearly indicates that ORM can induce differentiation in myeloid leukemia cells. It is noteworthy to mention here that at higher doses (5 uM to 7.5 uM) there is early onset of myeloid differentiation (72 h for 5 uM and 24,48 h for 7.5 uM) with reduced no. of cells which is likely due to apoptotic effects of ORM at higher dose. In contrary, at lower doses (1 uM) differentiation is observed after longer duration (6-15 days) with quite reduced apoptotic effect.

EXAMPLE-3

Confirmation of Differentiation with Biochemical Assay

Figure 3B:
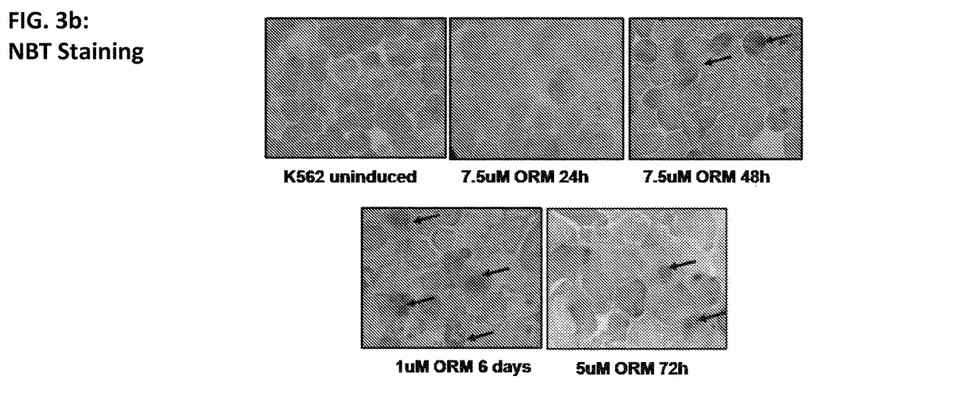

In order to further confirm the ORM induced differentiation in myeloid leukemia cells, Nitro Blue Tetrazolium (NBT) reduction assay is carried out which is a biochemical assay wherein activated granulocytes can reduce NBT to insoluble purple blue colour precipitates. Further, because ORM induces apoptosis at 7.5 uM in K562 cells; we treated K562 cells with 7.5 uM for 24 h and 48 hrs and 1 uM doses for longer duration, 6 days. Cells were subjected for NBT reduction analysis. As shown in the FIG. 3b, dramatic increase in NBT reduction marked by purple blue coloration in the ORM treated cells was observed. This further confirmed differentiation inducing potential of ORM.

Figure 5:
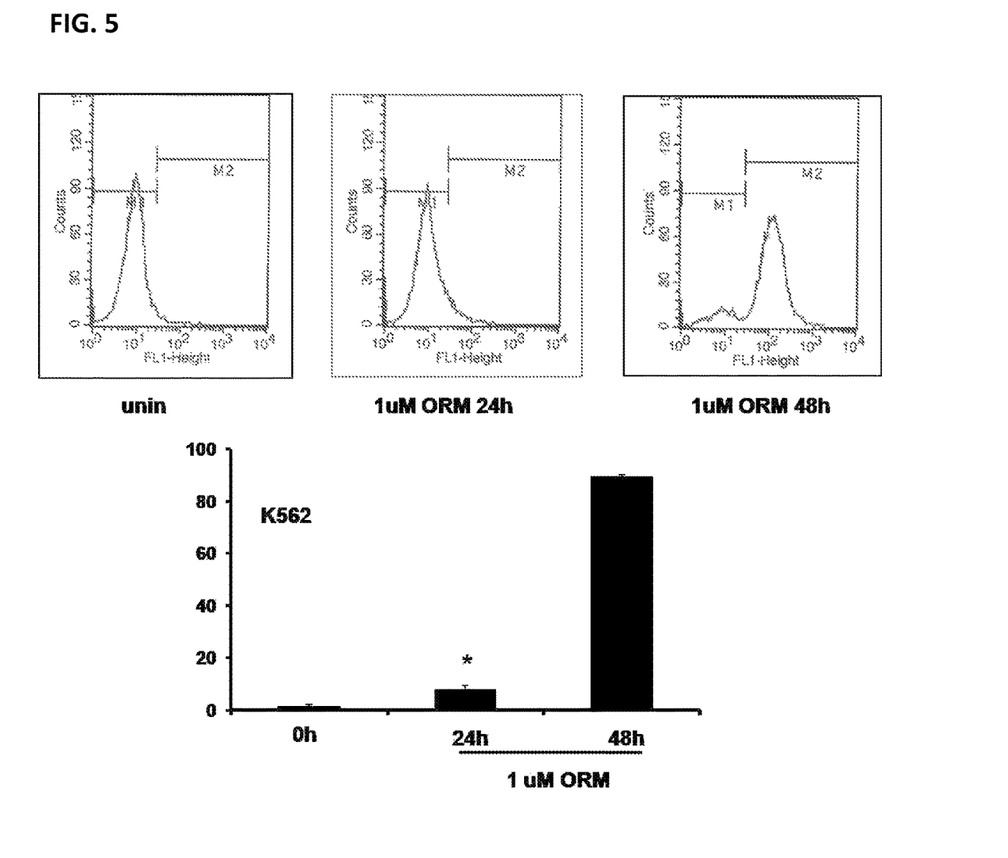
FIG. 5: ORM at a dose of 1 uM induces ROS generation: A property of activated neutrophils: Flow cytometry analysis was performed for the ROS generation in K562 cells after treatment with 1 uM ORM for 24 h and 48 h. Cells were labeled with DCF-DA dye and fluorescence was measured. A shift in the peak was observed in the K562 cells treated with 1 uM ORM after 48 h.

Furthermore, ORM induces granulocytic differentiation in K562 cells, it should lead to terminal differentiation of these cells to activated neutrophils. To substantiate further the induction of granulocytic differentiation and neutrophil formation, we measured the ROS generation, which is a property of activated neutrophils by FACS flow cytometer. Significant upregulation in ROS generation upon 1 uM ORM induction in K562 cells was observed (FIG. 5) which suggests ORM indeed induces granulocytic differentiation in these cells.

EXAMPLE-4

Figure 4A:
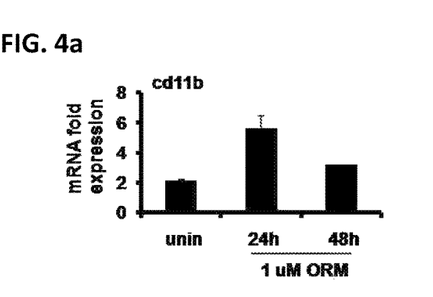
Figure 4B:
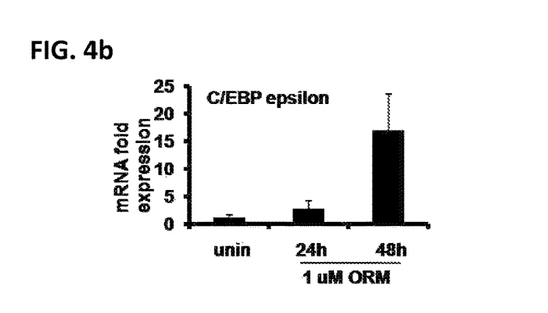
Figure 4C:
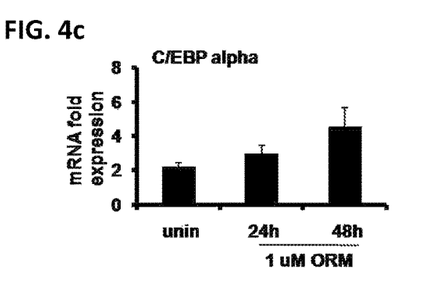
Figure 4D:
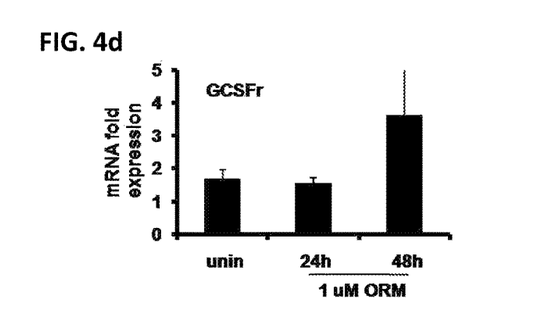
Figure 4E:
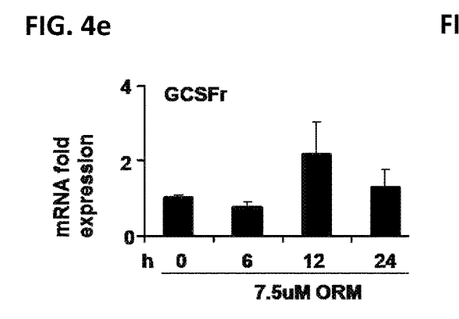
Figure 4F:
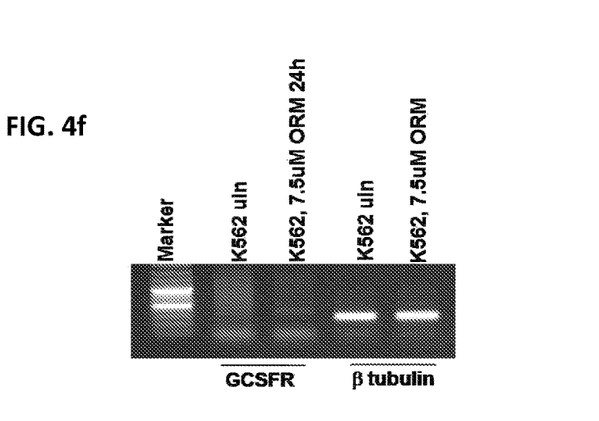
Figure 4G:
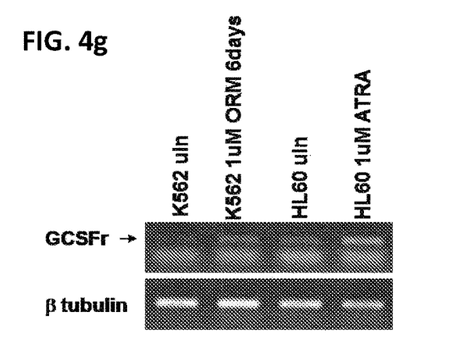

ORM Induced Differentiation in Myeloid Leukemia Cells Correlates with Enhanced Expression of Differentiation-Regulated Genes ORM induced myeloid differentiation was further demonstrated by assessing the changes in molecular markers of myeloid differentiation. Quantitative real time PCR from 1 uM ORM induced K562 cells (for 24 and 48 h) showed increased mRNA expression of cd11b (general myeloid differentiation marker (S. Koschmieder et. al.; Blood, 2007, 110(10):3695-3705), C/EBPalpha, C/EBP epsilon and GCSFr (markers of granulocytic differentiation; FIG. 4a,b, c,d). In addition, quantitative and semi quantitative PCR of 7.5 uM ORM treated K562 cells after 24 h and 48 h also showed modest upregulation of GCSFr (FIG. 4e, f) suggesting ORM does induces granulocytic differentiation in K562 cells. Expression of GSCFr expression after six days treatment with 1 uM ORM further demonstrated induction of differentiation in these cells (FIG. 4g).

EXAMPLE-5

Figure 6A:
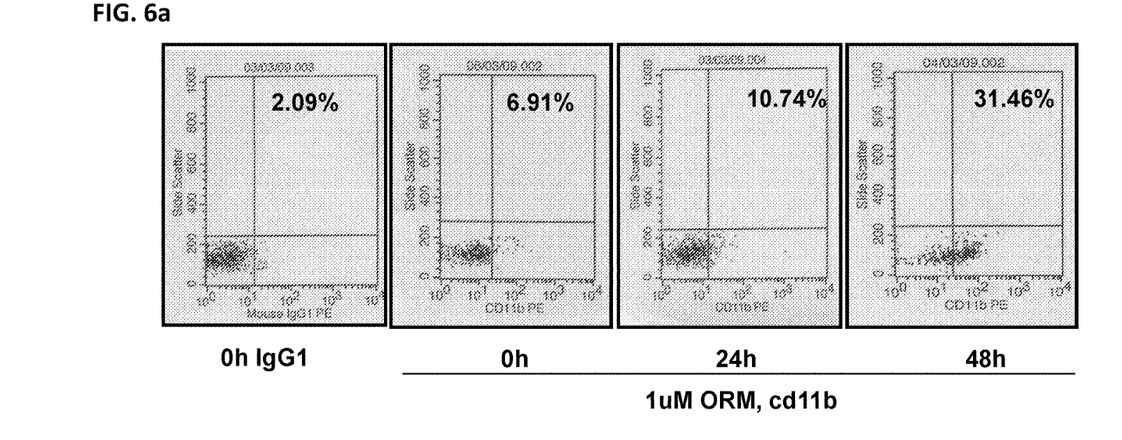
Figure 6B:
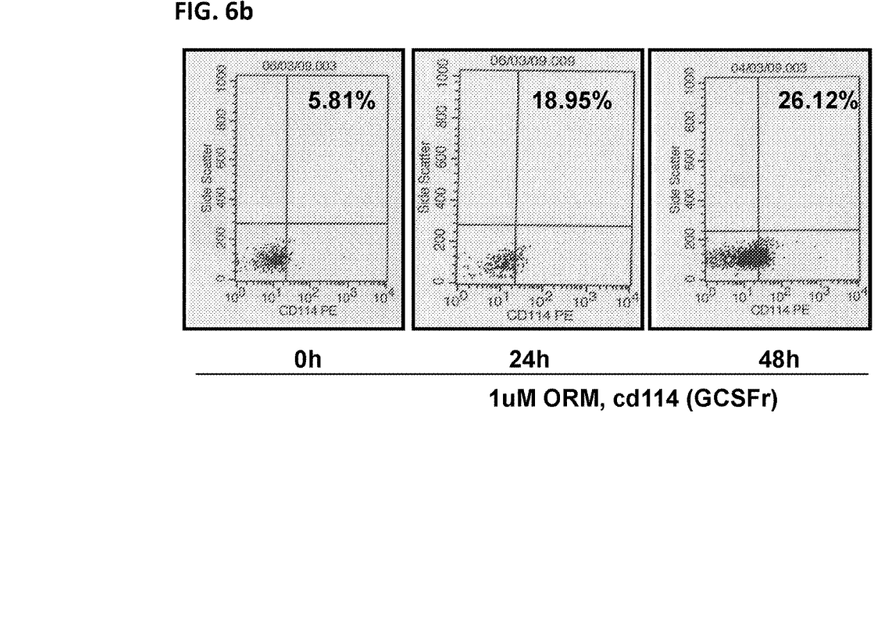
Figure 6C:
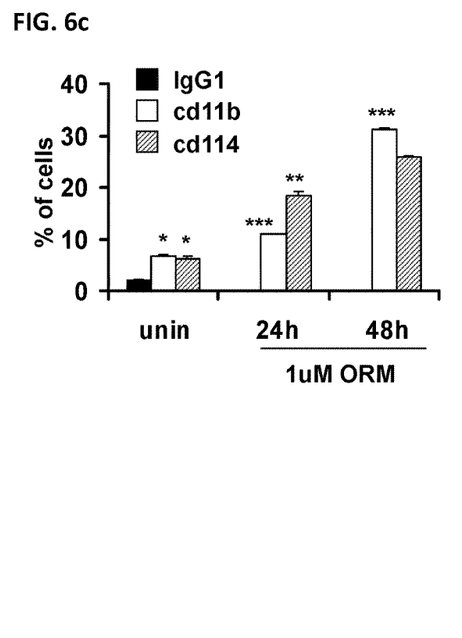

ORM Induces Myeloid Differentiation in Primary Cells Isolated from CML Patients Significant advances made in cancer therapy during the last decade as our understanding of molecular biology and leukemogenesis evolved, suggests that leukemic cell proliferation, apoptosis and differentiation should be targeted by anti leukemic agents. Although recent studies using differentiation therapies in oncology have been successful for acute promyelocytic leukemia (APL) with the use of all-trans retinoic acid (ATRA) (S. Waxman, Leukemia, 2000, 14(3):491-496), little is known about exact mechanisms of differentiation. Since. ORM profoundly induces granulocytic differentiation in K562 cells, we sought to assess if these in-vitro effects of ORM can be translated to primary cells isolated from chronic myeloid leukemia patients. 10 ml of peripheral blood upon prior consent of patients were drawn, mononuclear cells were separated using ficol-hypaq gradient centrifugation and cultured in RPMI supplemented with 10% FBS. 24 h post culture, cells were washed and plated at a density of $2\times10^5$ cells/ml. Cells were treated with 1 uM ORM and were analyzed for expression of cd11b and cd114 surface markers after 24 and 48 hr. As shown in FIG. 6a and b, significant upregulation in expression of myeloid and granulocytic differentiation markers were observed.

Taken together, these data show that the effects of ORM in myeloid cells can be translated in primary mononuclear cells isolated from CML patients.

EXAMPLE-6

ORM Induces Differentiation in HL60 and U937 Cells

Figure 7A:
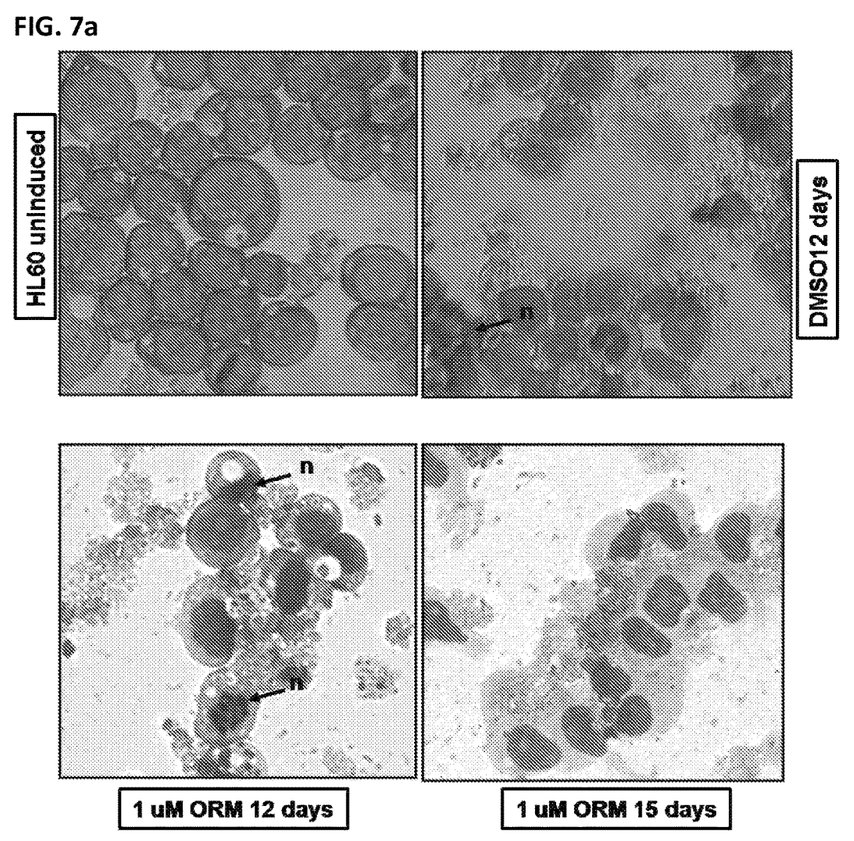
Figure 7B:
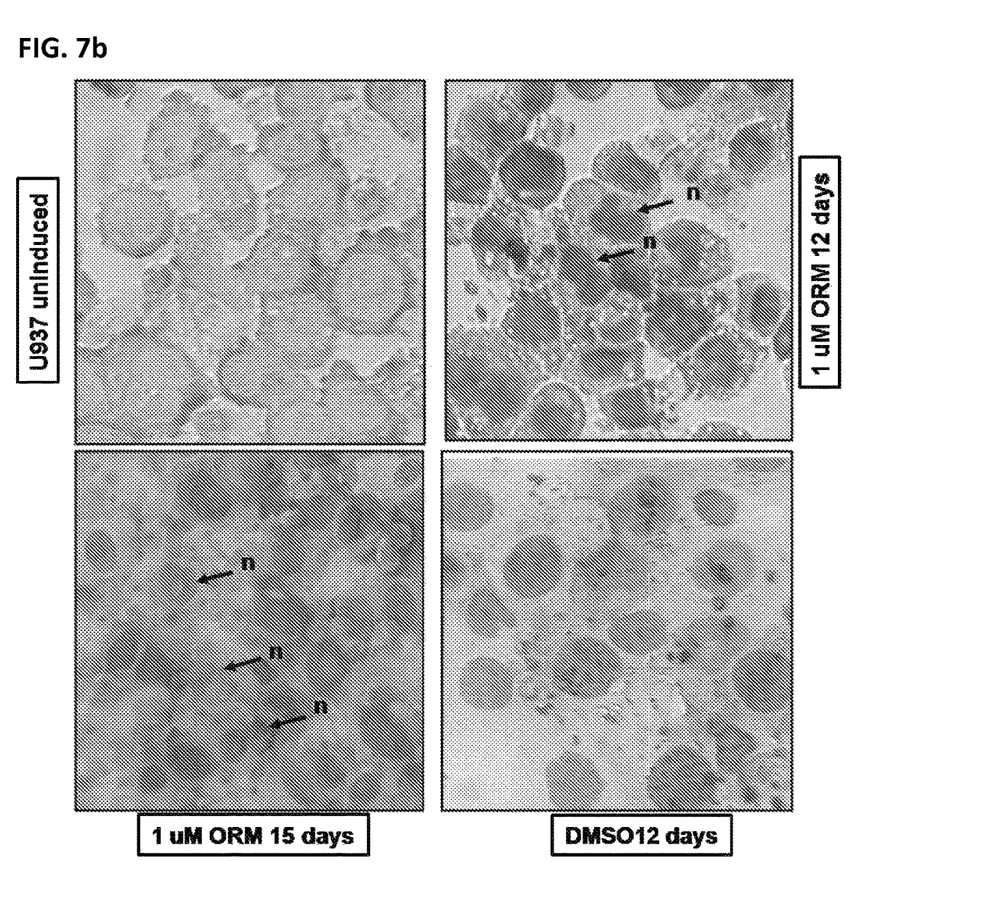

Profound granulocytic differentiation inducing property of ormeloxifene in K562 prompted us to investigate if ORM can also induce such differentiation in other myeloid leukemia cell lines. So we further chose HL60 and U937, a promyelocyte and myelomonocyte leukemia cell line. These cells differentiate to granulocyte lineage upon induction with all trans-retinoic acid (ATRA) and represent a very good model cell line for such differentiation assays. These cells were treated with 1 uM ORM for longer duration of 12 and 15 days followed by assessment of granulocytic/neutrophil like morphology. As seen in FIG. 7a,b large number of cells with multilobed nucleus, a feature of differentiated myeloid cells was observed suggesting ORM indeed promotes myeloid differentiation.

ADVANTAGES OF THE INVENTION

The new use of commercially available contraceptive as an antileukemic agent has several advantages; it is well established drug having well documented toxicity and other physiologically relevant pharmacological parameters. Since it is known to induce apoptosis and now we show that it also induces myeloid differentiation at varying doses well within toxicity limits, it offers a very good direct therapeutics either alone or in combination with other antileukemic drugs.

We claim:

1. A method for the treatment of a human having a myeloid leukemia, the method comprising:
    contacting a myeloid leukemia cell of the human with a subapoptotic concentration of ormeloxifene or salt thereof that induces differentiation in the myeloid leukemia cell, wherein the subapoptotic concentration is less than 5 µM and wherein the expression of cd11b markers in the cell is at least 10.74%.

2. The method of claim 1, wherein the subapoptotic concentration is 1.0 µM.

3. The method of claim 1, wherein the myeloid leukemia is an acute promyelocytic leukemia, an acute myeloid leukemia, or a chronic myelogenous leukemia.

4. The method of claim 1, wherein the myeloid leukemia is an acute promyelocytic leukemia.

5. The method of claim 1, wherein the myeloid leukemia is an acute myeloid leukemia.

6. The method of claim 1, wherein the myeloid leukemia is a chronic myeloid leukemia.

7. The method of claim 1, the induced differentiation is marked by an increase in C/EBPα, cd11b, and granulocyte colony stimulating factor receptor (GC SFr).

* * * * *